US011160692B2

(12) United States Patent
Utani et al.

(10) Patent No.: US 11,160,692 B2
(45) Date of Patent: Nov. 2, 2021

(54) METHOD AND APPARATUS FOR MANUFACTURING ABSORBENT ARTICLE

(71) Applicant: ZUIKO CORPORATION, Osaka (JP)

(72) Inventors: Kouji Utani, Osaka (JP); Daisuke Inoue, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 112 days.

(21) Appl. No.: 16/341,045

(22) PCT Filed: Sep. 21, 2017

(86) PCT No.: PCT/JP2017/034114
§ 371 (c)(1),
(2) Date: Apr. 10, 2019

(87) PCT Pub. No.: WO2018/079144
PCT Pub. Date: May 3, 2018

(65) Prior Publication Data
US 2019/0231607 A1    Aug. 1, 2019

(30) Foreign Application Priority Data

Oct. 31, 2016   (JP) .............................. JP2016-213077

(51) Int. Cl.
*A61F 13/00*   (2006.01)
*A61F 13/15*   (2006.01)
*A61F 13/49*   (2006.01)

(52) U.S. Cl.
CPC ........ *A61F 13/15723* (2013.01); *A61F 13/15* (2013.01); *A61F 13/15764* (2013.01);
(Continued)

(58) Field of Classification Search
CPC ......... A61F 13/49; B65G 47/244; B65H 5/12; B65H 2801/57
See application file for complete search history.

(56) References Cited

U.S. PATENT DOCUMENTS

| 6,602,007 B1* | 8/2003 | Majus | ................... B26D 7/1836 |
| | | | 400/616 |
| 9,011,405 B2* | 4/2015 | Gassner | ............ A61F 13/49017 |
| | | | 604/385.3 |

(Continued)

FOREIGN PATENT DOCUMENTS

| JP | S60-174147 A | 9/1985 |
| JP | H3-195555 A | 8/1991 |

(Continued)

OTHER PUBLICATIONS

International Search Report Issued in PCT/JP2017/034114 dated Dec. 12, 2017 (English translation).

*Primary Examiner* — Eyamindae C Jallow
(74) *Attorney, Agent, or Firm* — Renner, Otto, Boisselle & Sklar, LLP

(57) ABSTRACT

An apparatus for manufacturing an article including an absorbent body includes: first and second rolls, in cooperation with each other, for trimming a continuous laminate to be the absorbent body so as to successively form the narrowed portions along the continuous laminate; a third roll for rotating in contact with the second roll to receive the continuous laminate from the second roll; and a separating cutter for successively severing the continuous laminate being carried by the third roll into units of individual articles, thereby obtaining the absorbent body.

10 Claims, 5 Drawing Sheets

(52) U.S. Cl.
CPC ............... *A61F 13/49017* (2013.01); *A61F 2013/49082* (2013.01)

(56) References Cited

U.S. PATENT DOCUMENTS

| | | | | |
|---|---|---|---|---|
| 9,144,522 | B2* | 9/2015 | Ostertag | A61F 13/49011 |
| 2007/0074953 | A1* | 4/2007 | McCabe | B65G 47/848 |
| | | | | 198/377.08 |
| 2008/0176729 | A1* | 7/2008 | Anelli | B65H 45/28 |
| | | | | 493/360 |
| 2008/0196564 | A1* | 8/2008 | McCabe | B26D 1/425 |
| | | | | 83/23 |
| 2009/0178755 | A1* | 7/2009 | Hornung | A61F 13/15593 |
| | | | | 156/91 |
| 2010/0192739 | A1* | 8/2010 | Piantoni | A61F 13/15764 |
| | | | | 83/26 |
| 2011/0251038 | A1* | 10/2011 | LaVon | A61F 13/15764 |
| | | | | 493/405 |
| 2012/0004087 | A1* | 1/2012 | Tharayil | B65H 37/00 |
| | | | | 493/461 |
| 2012/0184937 | A1* | 7/2012 | Sablone | A61F 13/15723 |
| | | | | 604/385.24 |
| 2012/0322639 | A1* | 12/2012 | Raidel | A61F 13/15699 |
| | | | | 493/334 |
| 2013/0152360 | A1* | 6/2013 | Schoultz | A61F 13/15756 |
| | | | | 29/428 |
| 2013/0239764 | A1* | 9/2013 | Mccabe | B26D 1/425 |
| | | | | 83/100 |
| 2013/0239765 | A1* | 9/2013 | Mccabe | B65H 39/14 |
| | | | | 83/100 |
| 2013/0270067 | A1* | 10/2013 | Papsdorf | B65G 47/847 |
| | | | | 198/377.01 |
| 2014/0109739 | A1 | 4/2014 | Schneider et al. | |
| 2014/0115757 | A1* | 5/2014 | Umebayashi | A61F 13/49 |
| | | | | 2/400 |
| 2014/0274646 | A1* | 9/2014 | Schneider | A61F 13/15756 |
| | | | | 493/379 |
| 2015/0083848 | A1* | 3/2015 | Yanez, Jr. | B65H 23/032 |
| | | | | 242/615 |
| 2015/0298927 | A1* | 10/2015 | Findley | B65H 19/123 |
| | | | | 242/559 |
| 2018/0362266 | A1* | 12/2018 | Schneider | B65G 47/244 |

FOREIGN PATENT DOCUMENTS

| | | |
|---|---|---|
| JP | 2011-506005 A | 3/2011 |
| JP | 2015-536831 A | 12/2015 |

\* cited by examiner

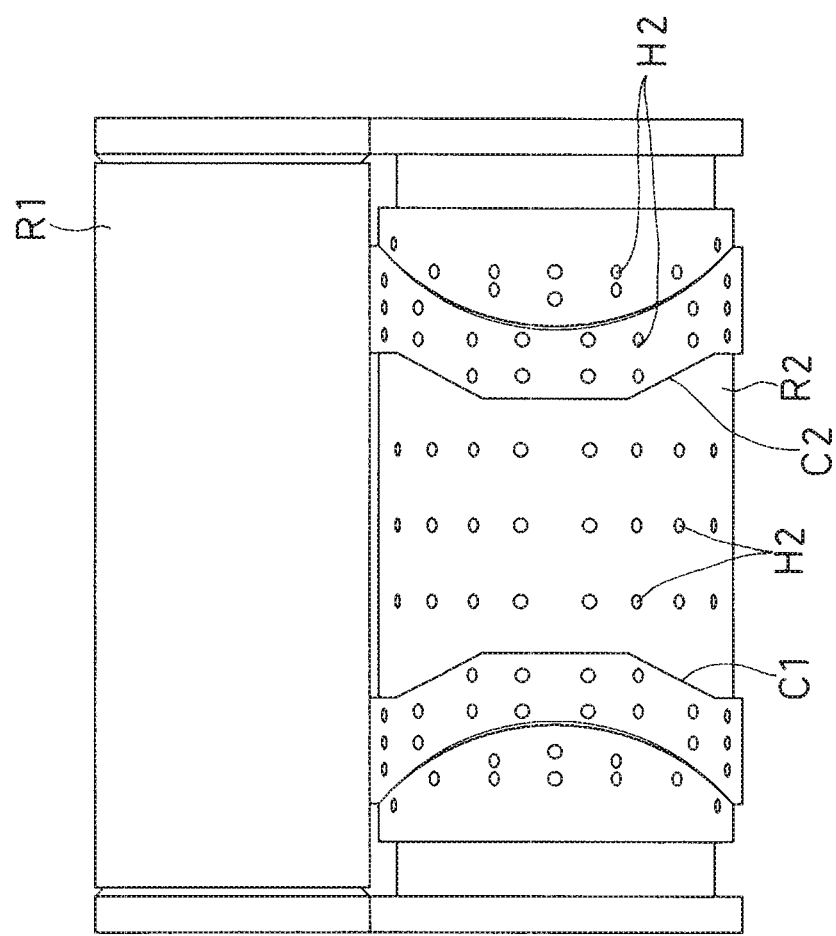

METHOD AND APPARATUS FOR MANUFACTURING ABSORBENT ARTICLE

TECHNICAL FIELD

The present invention relates to a method and an apparatus for manufacturing an absorbent article including an absorbent body having narrowed portions formed in the crotch portion.

BACKGROUND ART

According to the first patent document identified below, narrowed portions to be the crotch portion are formed along the continuous laminate of the absorbent body, after which it is severed into individual absorbent bodies. The carrying direction of each severed absorbent body is changed, and the absorbent body is placed on front and rear around-torso members.

CITATION LIST

Patent Literature

[First Patent Document] WO2009/080180 (front page)

SUMMARY OF INVENTION

However, creases are likely to be produced with this manufacturing method. The creases are likely to cause a defect when attaching the absorbent body to around-torso members or result in bad external appearance. Such problems are pronounced particularly when leg elastic members are placed on the absorbent body.

It is an object of the present invention to provide a method and an apparatus for manufacturing an absorbent article, with which creases are not produced on the absorbent body, thereby realizing desirable attachment of the absorbent body to around-torso members, while also improving the external appearance.

A manufacturing method of the present invention is a method for manufacturing an article including an absorbent body 2 having narrowed (constricted, necked) portions 211 to be a crotch portion 23, the method including:

an introduction step of introducing a continuous laminate W2 to be the absorbent body 2 into between a first roll R1 and a second roll R2;

a trimming step of trimming the continuous laminate W2 by the first and the second rolls R1 and R2 so as to successively form the narrowed portions 2H along the continuous laminate W2;

a first hand-over step of handing over the continuous laminate W2 from the second roll R2 to a third roll. R3; and a separation step of successively severing the continuous laminate W2 being carried by the third roll R3 into units of individual articles, thereby obtaining the absorbent body 2, wherein the method includes a first hold step of continuing to hold the continuous laminate W2 by at least one of the second roll R2 and the third roll R3, after trimming the continuous laminate W2 in the trimming step until the separation in the separation step.

A manufacturing apparatus of the present invention is an apparatus for manufacturing an article including an absorbent body 2 having narrowed (constricted, necked) portions 211 to be a crotch portion 23, the apparatus including:

first and second rolls R1 and R2, in cooperation with each other, for trimming a continuous laminate W2 to be the absorbent body 2 so as to successively form the narrowed portions 211 along the continuous laminate W2, wherein one of the first and second rolls R1 and R2 is a trim cutter and the other is a first anvil;

a third roll R3 for rotating in contact with the second roll R2 to receive the continuous laminate W2 from the second roll R2; and a separating cutter for successively severing the continuous laminate W2 being carried by the third roll. R3 into units of individual articles, thereby obtaining the absorbent body 2 that is one of the individual articles.

According to the present invention, after the trimming of the continuous laminate W2 until the separation, the continuous laminate W2 continues to be held by at least one of the second roll R2 and the third roll R3. Therefore, creases will not be produced on the trimmed continuous laminate W2.

Therefore, the absorbent body 2 will later be reliably attached to the around-torso members. Creases are unlikely to be produced, thereby improving the external appearance of the absorbent article (worn article).

Herein, "hold the continuous laminate W2" means to maintain the state in which the continuous laminate W2 is stretched in the longitudinal direction, which is the carrying direction, and the holding of the continuous laminate W2 is realized commonly by applying a tension on the continuous laminate W2 in the longitudinal direction of the continuous laminate W2.

The continuous laminate W2 includes a plurality of absorbent bodies, which are obtained by the separation step, continuous together in the carrying direction.

BRIEF DESCRIPTION OF DRAWINGS

FIG. 5 is a schematic plan view showing first and second rolls.

DESCRIPTION OF EMBODIMENTS

Figure 1:
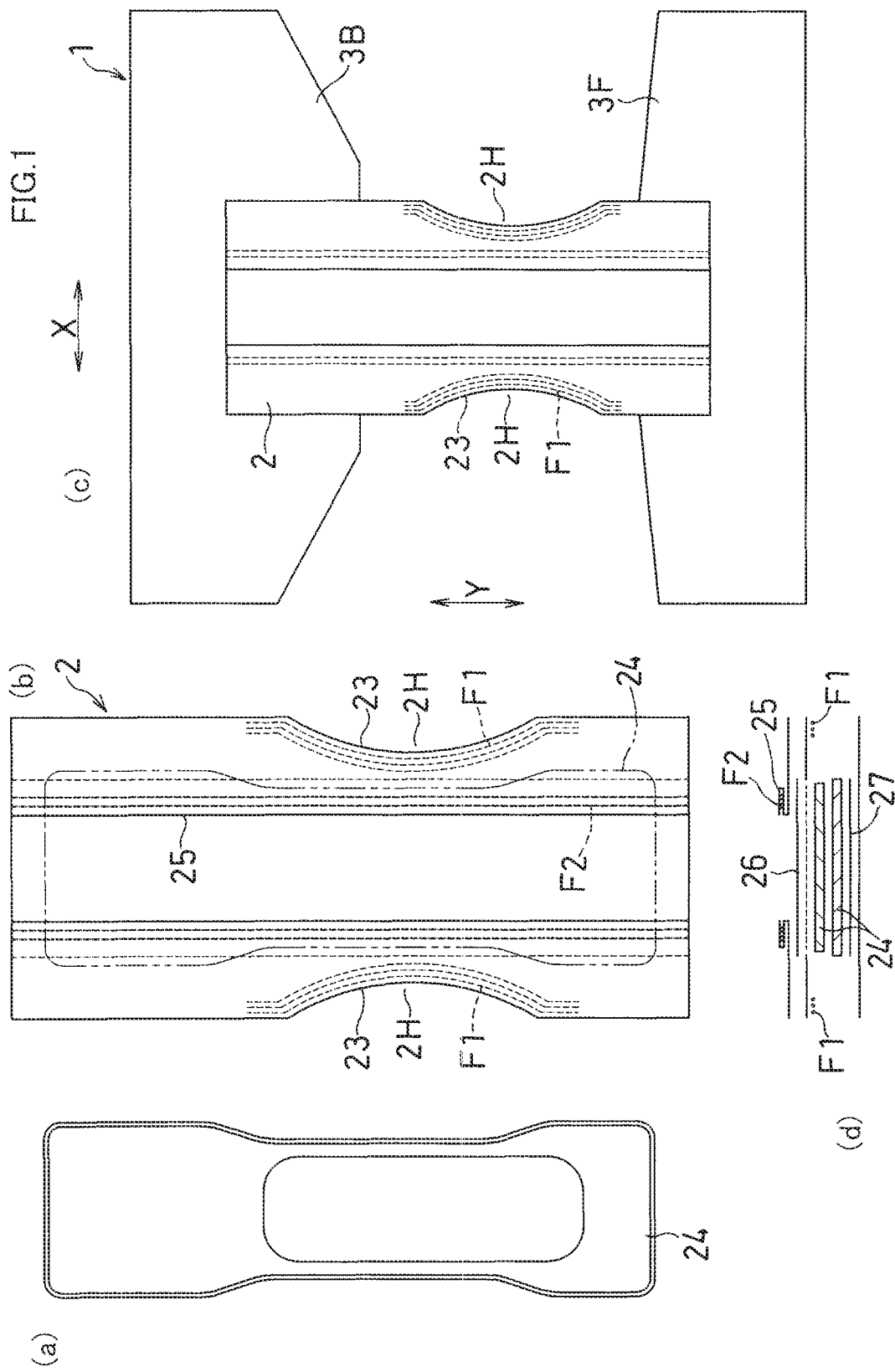
FIGS. 1(*a*) to 1(*d*) are plan views of an absorbent core of a worn article (absorbent article) to which the present invention is applied, an absorbent body using the same, and the worn article, and a cross-sectional view of the absorbent body, respectively.

Preferably, the method of the present invention further includes, prior to the introduction step, a step of placing, on the continuous laminate W2, a leg elastic member F1 that is stretchable in a longitudinal direction of the absorbent body 2.

Preferably, the apparatus of the present invention further includes a pair of nip rolls Rn for sandwiching an elastic member to be a leg elastic member F1 between a pair of webs W0 and W1 to be the continuous laminate W2.

Thus, although the continuous laminate W2 including the leg elastic member F1 placed therein is urged to shrink in the longitudinal direction, inadvertent shrinking of the continuous laminate W2 is suppressed by the holding.

More preferably, the method of the present invention further includes:

a second hand-over step of handing over the absorbent body 2 separated in the separation step from the third roll R3 to a hold pad P of a placement drum D; and a second hold step of continuing to hold the absorbent body 2 by at least one of the third roll R3 and the hold pad P, in the second hand-over step.

More preferably, the apparatus of the present invention further includes:

a placement drum D for receiving the separated absorbent body 2 from the third roll R3, wherein the third roll R3 includes a hold device B for continuing to hold a tip portion of the continuous laminate W2 before being severed by the separating cutter, and the absorbent body 2 having been severed by the separating cutter until the absorbent body 2 is handed over to the placement drum D.

In this case, the state in which the absorbent body 2 is held is maintained by at least one of the third roll R3 and the pad P. Therefore, creases will not be produced on the individually trimmed absorbent bodies 2.

Therefore, the absorbent body 2 will be reliably attached to the around-torso members. Creases are unlikely to be produced, thereby improving the external appearance of the absorbent article.

Herein, "hold the absorbent body 2" means to maintain the state in which the absorbent body 2 is stretched in the longitudinal direction, which is the carrying direction, and the holding of the absorbent body 2 is realized commonly by using a negative pressure, or the like, so as to suck the absorbent body 2 onto the third roll R3 or the pad P.

More preferably, the method of the present invention further includes an attitude changing step in which the hold pad P on the placement drum D turns about a normal L to the placement drum D, thereby changing an attitude of the absorbent body 2 on the hold pad P.

More preferably, in the apparatus of the present invention, the placement drum D includes a hold pad P for receiving the absorbent body 2 from the third roll R3 and turning about a normal to the placement drum D, thereby changing an attitude of the received absorbent body 2.

In these cases, creases will not be produced on the absorbent body when the hold pad of the placement drum changes the attitude of the absorbent body.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

The structure of a worn article 1 according to one embodiment of the present invention will now be described with reference to the drawings.

As shown in FIG. 1(*c*), the worn article 1 of the present embodiment includes an absorbent body 2, a front around-torso member 3F and a rear around-torso member 3B. The absorbent body 2 includes a crotch portion 23 that covers the crotch of the wearer.

The crotch portion 23 extends in the longitudinal direction Y perpendicular to the girth direction X. The absorbent body 2 forms a part or whole of the crotch portion 23.

When worn, the crotch portion 23 is folded in two along a line that is parallel to the girth direction X. Thus, the end portion of the front around-torso member 3F in the girth direction X and that of the rear around-torso member 3B overlap with each other.

An absorbent core 24 of FIG. 1(*a*) is provided in the absorbent body 2 of FIG. 1(*b*), and the absorbent core 24 absorbs a bodily fluid. The absorbent core 24 of FIG. 1(*d*) is sandwiched between a top sheet 26 and a back sheet (resin sheet) 27, and the sheets 26 and 27 and the absorbent core 24 are layered together.

The top sheet 26 is formed from a permeable non-woven fabric, and covers the skin-contact surface of the absorbent core 24. A pair of three-dimensional cuffs 25 are provided on the top sheet 26. Note that the back sheet 27 covers the non-skin-contact surface of the absorbent core 24 and is formed from a liquid-impermeable resin sheet.

In FIG. 1(*c*), the absorbent body 2 is provided so as to bridge between the front around-torso member 3F and the rear around-torso member 3B.

As shown in FIG. 1(*b*), narrowed (constricted) portions 2H that are narrowed along the legs of the wearer may be formed along the absorbent body 2. A leg elastic member F1 made of a rubber thread, or the like, may be provided in the narrowed portions 2H so as to conform around the legs of the wearer. The leg elastic member F1 may be placed over a part or whole of the absorbent body 2 in the longitudinal direction. There may be a plurality of leg elastic members F1 placed on both sides of the absorbent body 2 along the narrowed portions 2H.

As shown in FIG. 1(*d*), in the present embodiment, the three-dimensional cuffs 25 are each formed to include a cuff elastic member F2, which is stretchable in the longitudinal direction Y, placed along its free-end-side edge.

When a worn article is a diaper, a pair of male touch fasteners (not shown) may be fixed to opposite edges of the skin-contact surface of the rear around-torso member 3B, and female touch fasteners may be fixed to the non-skin-contact surface of the front around-torso member 3F.

Note that a tape material with a fastening agent applied thereon may be used instead of the male touch fasteners. In this case, the front around-torso member 3F, etc., needs to be provided with a surface on which the fastening agent adheres easily.

When the worn article is pants-shaped, the end portion in the girth direction X of the front around-torso member 3F and that of the rear around-torso member 3B may be welded to each other.

The non-skin-contact surface of the around-torso members 3F and 3B of FIG. 1(*c*) is made of a non-woven fabric.

In the present specification, the "skin-contact surface" refers to a surface that faces the skin of the wearer when the worn article 1 is worn, and the "non-skin-contact surface" refers to the surface opposite to the skin-contact surface.

Next, one embodiment of the manufacturing apparatus will be described with reference to FIG. 3 to FIG. 5.

The present manufacturing apparatus of FIG. 8 includes a pair of nip rolls Rn, first to third rolls R1 to R3, a separating cutter C, the placement drum D, a carrying device T, etc.

The pair of nip rolls Rn nips an elastic member to be the leg elastic member F1 between a pair of webs W0 and W1 to be a continuous laminate W2.

The first roll R1 is a first anvil roll, for example.

The second roll R2 is a trim cutter roll, for example.

Figure 2:
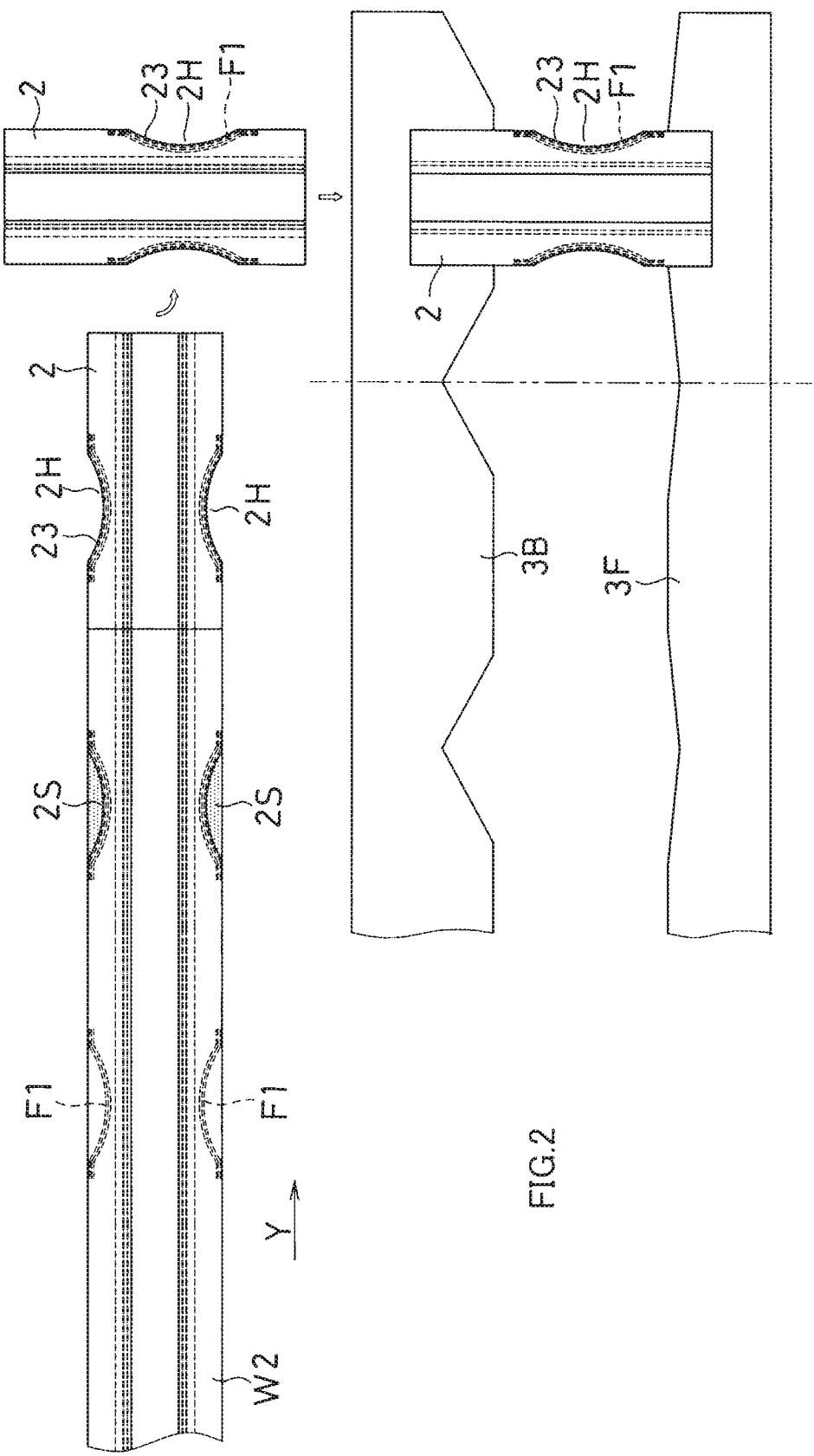
FIG. 2 is a schematic plan view showing one embodiment of a manufacturing method of the present invention.

These rolls R1 and R2, in cooperation with each other, trim the continuous laminate W2 to be the absorbent body 2 of FIG. 2 so as to successively form the narrowed portions 2H along the continuous laminate W2. The narrowed (constricted, necked) portions 2H are formed along both edges of the continuous laminate W2. Note that the narrowed portions 2H are formed along the leg elastic members F1.

As shown in FIG. 5, the first and second rolls R1 and R2 may be in contact with each other at their opposite ends. Many suction holes H2 are formed on the surface of the second roll R2 for sucking the trimmed absorbent body 2 and scraps 2S of FIG. 2.

In FIG. 5, in the case of the present embodiment, the diameter of the first (anvil) roll R1 is smaller than the diameter of the second roll (trim cutter roll) R2.

Blades C1 and C2 corresponding to the integral number of absorbent bodies 2 (FIG. 1) (one in the present embodiment) are provided on the circumferential surface of the trim cutter roll R2. In the present embodiment, per each revolution of the trim cutter roll R2, a pair of narrowed portions 2H (FIG. 2) are formed for a portion of the continuous laminate that accounts for one absorbent body 2. Therefore, the diameter of the second roll R2 of the present embodiment is the minimum diameter for a trim cutter roll for trimming the absorbent body 2.

Figure 4:
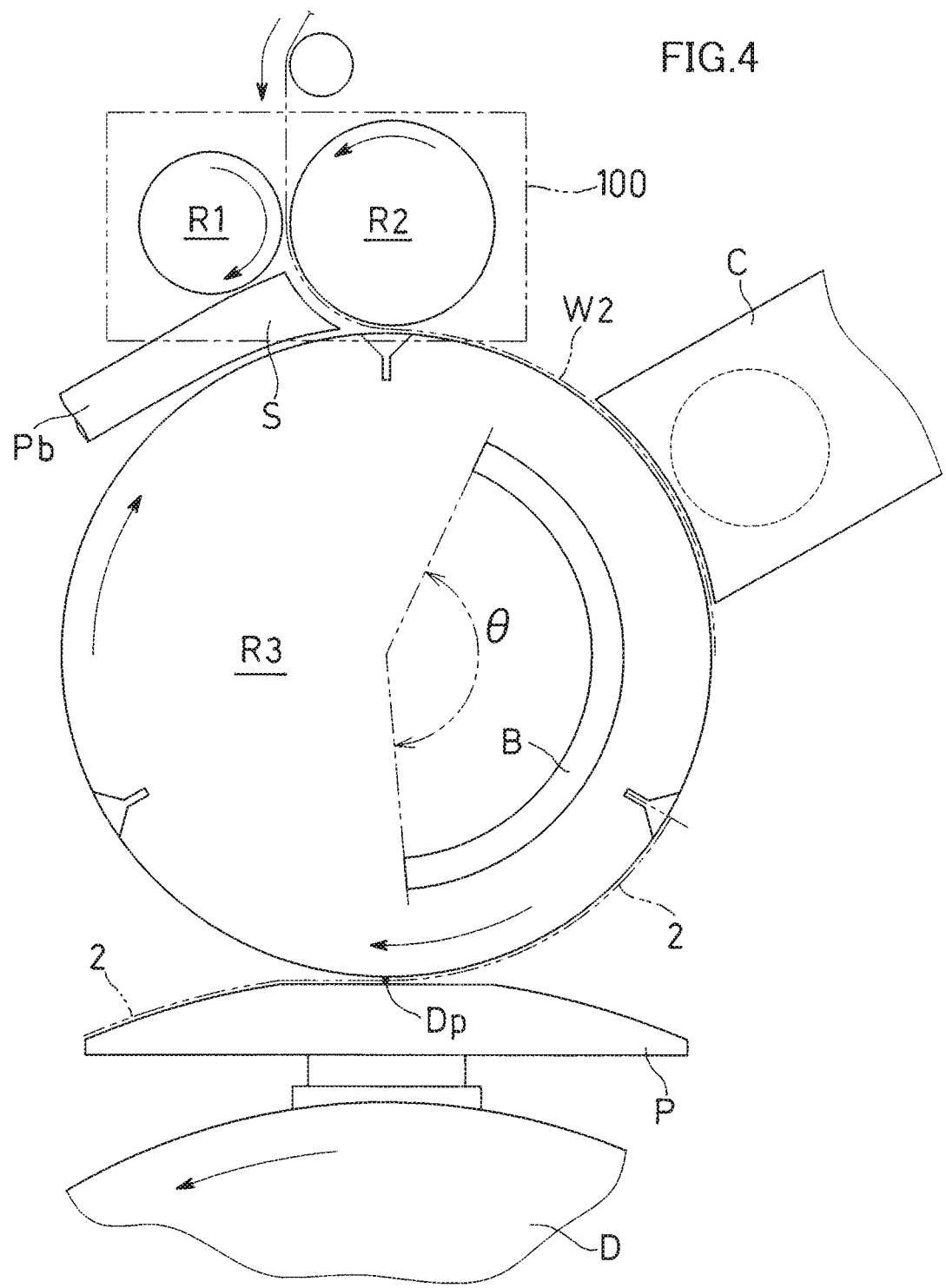
FIG. 4 is a schematic layout diagram showing first to third rolls and a hold pad.

In FIG. 4, a suction pipe Pb is placed between the first anvil roll R1 and the third roll R3. That is, a tip portion of the suction pipe Pb is placed in the space S that is formed between the first anvil roll R1, the trim cutter roll R2 and the third roll R3. The suction pipe Pb sucks away scraps of the continuous laminate W2 that are produced when trimming by the trim cutter roll R2.

Note that the first and second rolls R1 and R2 are supported on a frame 100, which is indicated by a two-dot-chain line.

Herein, the space S is produced because the diameter of the first roll R1 is smaller than the diameter of the second roll R2, which is the minimum diameter. This space S can be used as a space where the suction pipe Pb is placed, thereby enabling a reduction in size of the manufacturing apparatus.

On the other hand, the first roll R1 may be a trim cutter roll and the second roll R2 may be an anvil roll. In this case, however, when one attempts to place the suction pipe Pb, the diameter of the second roll R2, which is an anvil roll, is greater than the diameter of the first roll R1, which is a trim cutter roll of the minimum diameter. Therefore, the size of the manufacturing apparatus will be larger than that of the embodiment of FIG. 4.

The third roll R3 rotates in contact with the second roll R2 to receive the continuous laminate W2 from the second roll R2. The circumferential speed of the third roll R3 is greater than the speed at which the continuous laminate W2 is carried. Therefore, the tip portion of the continuous laminate W2 is carried by being sucked by the hold device B of the third roll R3, while slipping on the third roll R3.

The separating cutter C successively severs the continuous laminate W2 being carried on the third roll R3 into units of individual articles, thereby obtaining absorbent bodies 2. The absorbent body 2, which is no longer continuous after being severed, is carried at the circumferential speed of the third roll R3, and the severed absorbent body 2 is therefore spaced away from the continuous laminate W2 in the circumferential direction of the third roll R3.

In FIG. 4, the third roll R3 includes the hold device B. The hold device B continues to hold the tip portion of the continuous laminate W2 before being severed by the separating cutter, and the absorbent body 2 having been severed by the separating cutter C, until the absorbent body 2 is handed over to a hold pad P of the placement drum D.

Although the structure is well known in the art, the hold device B of the third roll R3 has a vacuum area θ over which the continuous laminate W2 or the absorbent body 2 is sucked onto the area of the angle θ of the third roll R3 via a vacuum.

The placement drum D receives the separated absorbent body 2 from the third roll R3.

Figure 3:
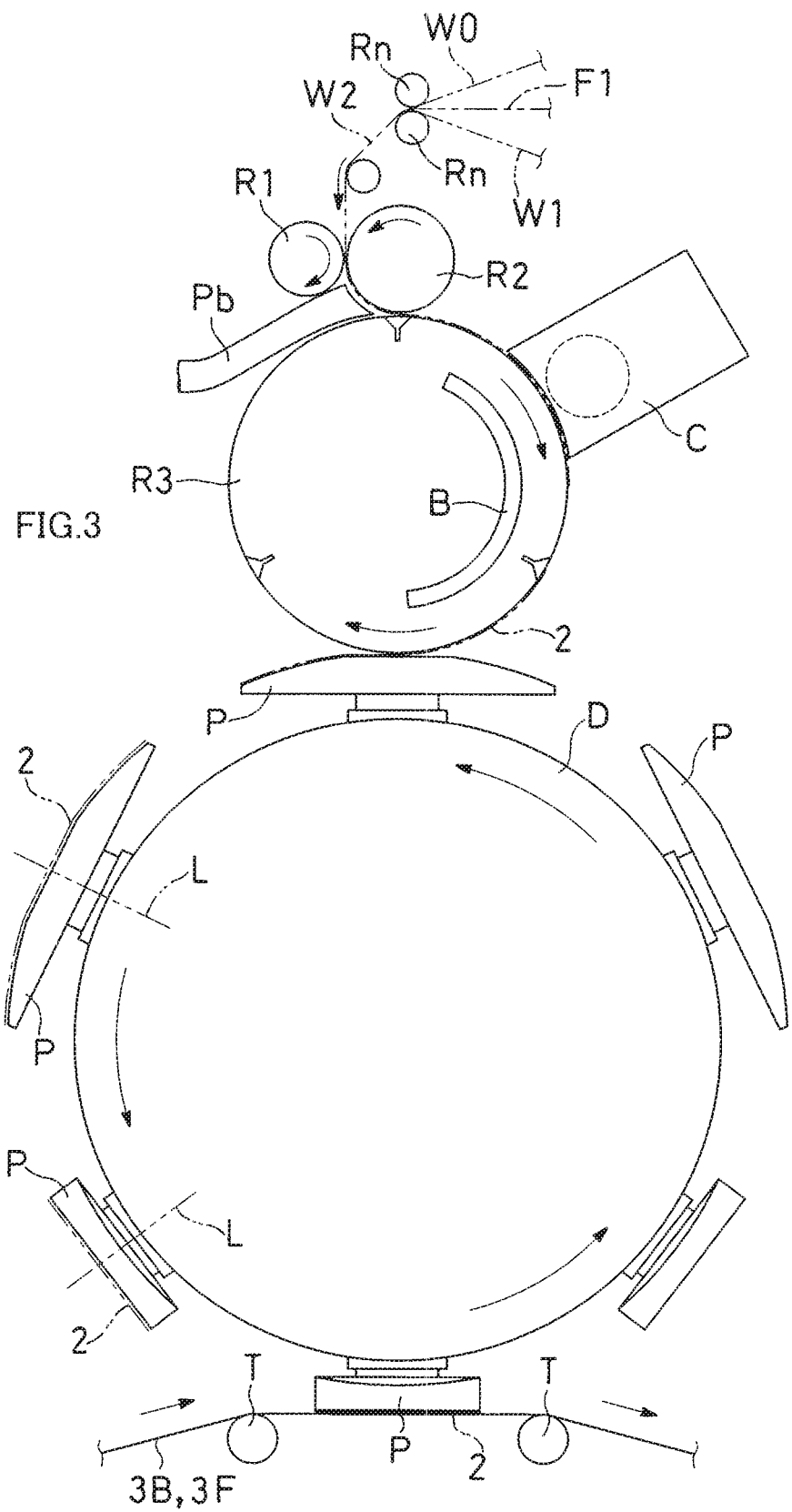
FIG. 3 is a schematic layout diagram showing one embodiment of a manufacturing method of the present invention.

As shown in FIG. 3, the placement drum D includes a plurality of hold pads P. The hold pad P receives the absorbent body 2 from the third roll R3, and turns about the normal L to the placement drum D, thereby changing the attitude of the received absorbent body 2.

The hold pad P may include a suction device. The suction device sucks the absorbent body 2 via a vacuum through many suction holes running through the surface of the pad, for example.

The placement drum D places the absorbent body 2, whose attitude has been changed, between a pair of a front around-torso member 3F and a rear around-torso member SB of FIG. 2 being carried by the carrying device T. In this process, with an adhesive applied in advance on the absorbent body 2, the absorbent body 2 is bonded to the front around-torso member SF and the rear around-torso member 8B.

Next, one embodiment of the manufacturing method will be described.

First, the leg elastic member F1 is sandwiched between a pair of webs W0 and W1 of FIG. 3, thus placing the leg elastic member F1, which is stretchable in the longitudinal direction of the continuous laminate W2 (the longitudinal direction Y) of FIG. 2.

Then, the continuous laminate W2 of FIG. 3 is introduced into between the first roll R1 and the second roll R2 (introduction step). The continuous laminate W2 is trimmed by the rolls R1 and R2 as shown in FIG. 2, thereby successively forming the narrowed portions 2H along the continuous laminate W2 (trimming step). This trimming produces scraps 2S corresponding to the narrowed portions 2H. The scraps 2S are sucked by the suction pipe Pb of FIG. 8 and discharged out of the system.

After the trimming, the first hand-over step is performed by handing over the continuous laminate W2 from the second roll R2 to the third roll R3. Then, the separation step is performed by carrying the continuous laminate W2 on the third roll R3 and successively severing the continuous laminate W2 being carried into units of individual articles, thereby obtaining the absorbent bodies 2.

After the trimming of the continuous laminate W2 until the separation, the continuous laminate W2 continues to be held by at least one of the second roll R2 and the third roll R3 (first hold step).

That is, while the continuous laminate W2 is in contact with the second roll R2, the continuous laminate W2 is sucked and held by the second roll R2 through the suction holes H2 of the second roll R2 of FIG. 5. On the other hand, when the continuous laminate W2 is in contact with the third roll R3, the continuous laminate W2 is sucked and held by the third roll R3 by means of the hold device B of the third roll R3 of FIG. 4.

Note that after the continuous laminate W2 is severed to produce the absorbent body 2, the absorbent body 2 is carried to the hand-over position Dp to the placement drum D while being sucked and held by the hold device B of the third roll R3.

The separated absorbent body 2 is handed over to the hold pad P of the placement drum D from the third roll R3 (second hand-over step). In this second hand-over step, the absorbent body 2 continues to be held by at least one of the third roll R3 and the hold pad P (second hold step).

That is, while the absorbent body 2 is carried by the third roll R3, the absorbent body 2 is sucked and held by the hold device B of the third roll R3 of FIG. 4. On the other hand, while the absorbent body 2 is carried by the hold pad P of the placement drum D, the absorbent body 2 is sucked and held by suction holes (not shown) of the hold pad P.

While the absorbent body 2 of FIG. 3 is sucked and held on the hold pad P, the hold pad P on the placement drum D turns about the normal L to the placement drum D, thereby changing the attitude of the absorbent body 2 as shown in FIG. 2 (attitude changing step).

Then, the absorbent body 2 is provided so as to bridge between the pair of around-torso members 3F and 3B. After the provision, the pair of around-torso members 3F and 3B are successively severed into units of individual worn articles along the sever line indicated by a two-dot-chain line.

While preferred embodiments have been described above with reference to the drawings, obvious variations and modifications will readily occur to those skilled in the art upon reading the present specification.

For example, the present worn article does not need to have cuffs. The trim cutter roll may be provided with blades such that a pair of narrowed portions is formed for each of two or more absorbent bodies per each revolution of the trim cutter roll. Thus, such changes and modifications are deemed to fall within the scope of the present invention, which is defined by the appended claims.

INDUSTRIAL APPLICABILITY

The present invention is applicable to the manufacture of various worn articles such as disposable pants and diapers.

REFERENCE SIGNS LIST

1: Worn article
2: Absorbent body, 2H: Narrowed (constricted) portion, 2S: Scrap, 23: Crotch portion, 24: Absorbent core
25: Three-dimensional cuff, 26: Top sheet, 27: Back sheet (resin sheet)
3F: Front around-torso member, 3B: Rear around-torso member
B: Hold device, C: Separating cutter, C1: Blade, D: Placement drum
F1: Leg elastic member, F2: Cuff elastic member
H2: Suction hole
W0, W1: Pair of webs, W2: Continuous laminate
X: Girth direction, Y: Longitudinal direction
P: Hold pad, Pb: Suction pipe
R1 to R3: First to third rolls, Rn: Nip roll
L: Normal, S: Space, T: Carrying device

The invention claimed is:

1. A method for manufacturing an article including an absorbent body having constricted portions to be a crotch portion, the method comprising:

an introduction step of introducing a continuous laminate to be the absorbent body into between a first roll and a second roll;

a trimming step of trimming the continuous laminate by the first and the second rolls so as to successively form the constricted portions along the continuous laminate;

a first hand-over step of handing over the continuous laminate from the second roll to a third roll, the third roll being in abutment with the second roll, wherein the continuous laminate is carried through a point of abutment between the third roll and the second roll; and a separation step of successively severing the continuous laminate being carried by the third roll into units of individual articles, thereby obtaining the absorbent body, wherein the method comprises a first hold step of continuing to hold the continuous laminate by at least one of the second roll and the third roll, after trimming the continuous laminate in the trimming step until the separation in the separation step.

2. The method for manufacturing an article according to claim 1, further comprising, prior to the introduction step, a step of placing, on the continuous laminate, a leg elastic member that is stretchable in a longitudinal direction of the absorbent body.

3. The method for manufacturing an article according to claim 1, further comprising:

a second hand-over step of handing over the absorbent body separated in the separation step from the third roll to a hold pad of a placement drum; and a second hold step of continuing to hold the absorbent body by at least one of the third roll and the hold pad, in the second hand-over step.

4. The method for manufacturing an article according to claim 3, further comprising an attitude changing step in which the hold pad on the placement drum turns about a normal to the placement drum, thereby changing an attitude of the absorbent body on the hold pad.

5. An apparatus for manufacturing an article including an absorbent body having constricted portions to be a crotch portion, the apparatus comprising:

first and second rolls, in cooperation with each other, for trimming a continuous laminate to be the absorbent body so as to successively form the constricted portions along the continuous laminate, wherein one of the first and second rolls is a trim cutter and another of the first and second rolls is a first anvil;

a third roll for rotating in abutment with the second roll to receive the continuous laminate from the second roll, wherein the continuous laminate is carried through a point of abutment between the third roll and the second roll; and a separating cutter for successively severing the continuous laminate being carried by the third roll into units of individual articles, thereby obtaining the absorbent body.

6. The apparatus for manufacturing an article according to claim 5, further comprising a pair of nip rolls for sandwiching an elastic member to be a leg elastic member between a pair of webs to be the continuous laminate.

7. The apparatus for manufacturing an article according to claim 5, further comprising:

a placement drum for receiving the separated absorbent body from the third roll, wherein the third roll includes a hold device for continuing to hold a tip portion of the continuous laminate before being severed by the separating cutter, and the absorbent body having been severed by the separating cutter until the absorbent body is handed over to the placement drum.

8. The apparatus for manufacturing an article according to claim 7, wherein the placement drum includes a hold pad for receiving the absorbent body from the third roll and turning about a normal to the placement drum, thereby changing an attitude of the absorbent body received from the third roll.

9. The apparatus for manufacturing an article according to claim 5, wherein:
   the first roll is a first anvil roll;
   the second roll is a trim cutter roll;
   a diameter of the first anvil roll is smaller than a diameter of the trim cutter roll; and
   a suction pipe for sucking away scraps that are produced when trimming the continuous laminate by the trim cutter roll is arranged between the first anvil roll and the third roll.

10. The apparatus for manufacturing an article according to claim 9, wherein blades corresponding to an integral number of the absorbent bodies are provided on a circumferential surface of the trim cutter roll.

\* \* \* \* \*